United States Patent [19]

Atchison

[11] 4,231,358
[45] Nov. 4, 1980

[54] SURGICAL DRESSING

[76] Inventor: Cheryle M. Atchison, 2629 N. Fruitdale Ave., Indianapolis, Ind. 46224

[21] Appl. No.: 959,319

[22] Filed: Nov. 9, 1978

Related U.S. Application Data

[63] Continuation of Ser. No. 731,042, Oct. 8, 1976, abandoned.

[51] Int. Cl.³ ............................................. A61F 13/00
[52] U.S. Cl. ................................. 128/168; 128/171; 128/289
[58] Field of Search ................ 128/98, 168, 171, 284, 128/289–290, 291, 292

[56] References Cited

U.S. PATENT DOCUMENTS

| | | | |
|---|---|---|---|
| 964,267 | 7/1910 | Johnson | 128/289 |
| 1,331,042 | 2/1920 | Andreae | 128/289 |
| 2,545,224 | 3/1951 | Butler | 128/289 |
| 2,615,445 | 10/1952 | Holmes | 128/98 |
| 2,928,394 | 3/1960 | Roberts | 128/289 |
| 3,227,160 | 1/1966 | Younger | 128/291 |
| 3,247,846 | 4/1966 | Fansler | 128/171 |
| 3,554,196 | 1/1970 | Wargo | 128/291 |
| 4,059,103 | 11/1977 | Glaser | 128/98 |

FOREIGN PATENT DOCUMENTS

| | | | |
|---|---|---|---|
| 223318 | 2/1962 | Austria | 128/291 |
| 291995 | 12/1931 | Italy | 128/168 |

*Primary Examiner*—C. Fred Rosenbaum
*Attorney, Agent, or Firm*—Woodard, Weikat, Emhardt & Naughion

[57] ABSTRACT

A surgical dressing arrangement is disclosed herein which comprises a pad having an integral layer of absorbent material sized to fit the perineal area of a person. The pad is generally rectangular and an attaching flap is connected to the rear of the pad. The flap extends and is secured to the person by attachment to a belt or by other suitable means. A strap is attached to each corner of the front end of the pad and each extends and is secured, for example, to the belt. A portion of the straps adjacent the pad may comprise a layer of absorbent material, which may be integral with the absorbent material of the pad.

4 Claims, 5 Drawing Figures

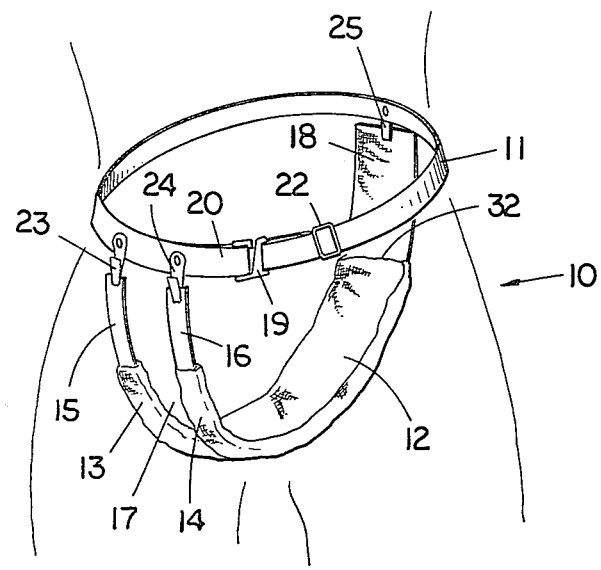
Fig.1
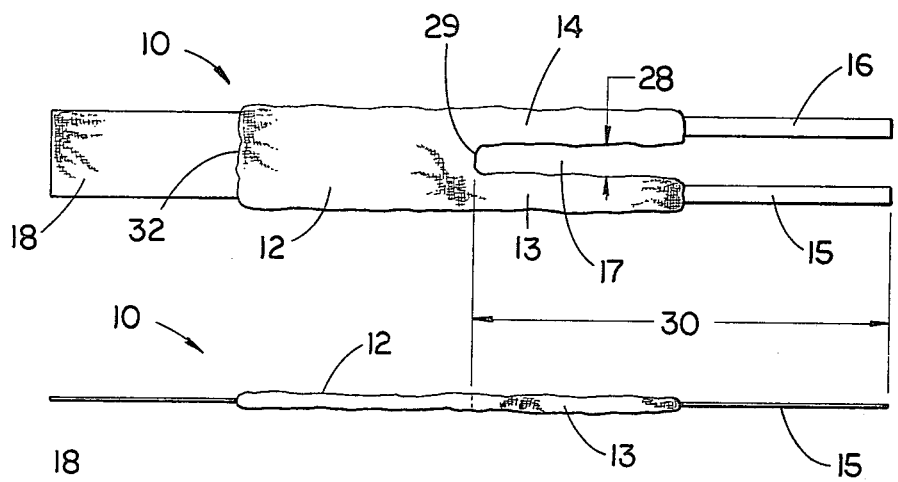
Fig.2
Fig.3
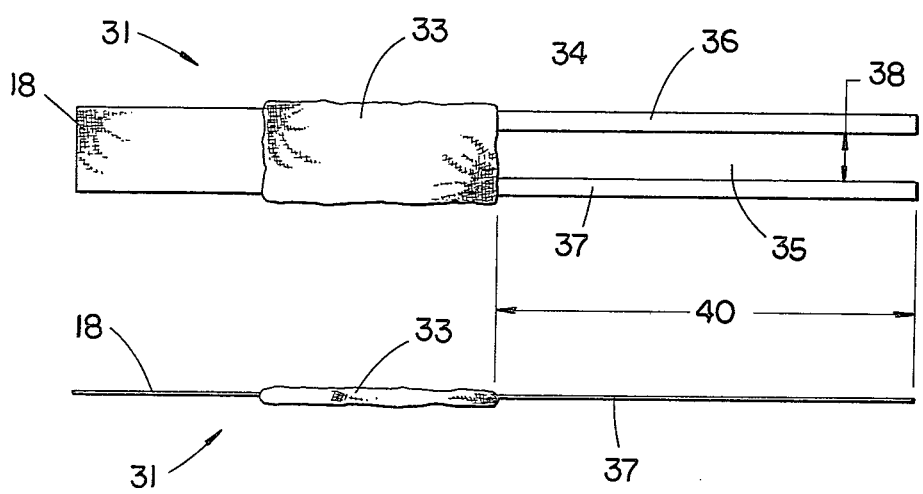
Fig.4
Fig.5

SURGICAL DRESSING

This is a continuation of application Ser. No. 731,042, filed Oct. 8, 1976 and now abandoned.

BACKGROUND OF THE INVENTION

1. Field of the Invention

This invention relates to a device for positioning a surgical dressing in the perineal area of a person, and more particularly to a device of the described type which does not employ separate dressing and support components.

2. Description of the Prior Art

Surgical belts and dressing supports are known in the prior art. These supports, however, have generally been relatively bulky and therefore uncomfortable to wear for any substantial length of time. The problem has also existed that the known support arrangements have not always been successful in maintaining the dressing firmly in place. Further, a disadvantage of certain of the prior art devices has been the inability to readily change the dressing.

In U.S. Pat. No. 2,684,673, issued to Lerman on July 27, 1954, there is disclosed a surgical dressing support designed to position a dressing in the perineal area. The support comprises a generally rectangular piece of material having one end attached to a strap, the strap in use being tied around the wearer's waist to form a belt. The rectangular portion is then drawn between the wearer's legs to the front of the person where it is secured to the belt by passing the straps through slots in the end of the rectangular portion. Similar devices are disclosed in U.S. Pat. Nos. 3,227,160, issued to Younger on Jan. 4, 1966; 3,247,846, issued to Fansler on Apr. 26, 1966; and, 2,545,223, issued to Butler on Mar. 13, 1951. In each of these devices, the support is of considerable bulk, and is used as a means for positioning a dressing which is separate therefrom, but which is pressed against the person by the rectangular portion of the support.

A comparable field of art is that which relates to the sanitary belt-napkin arrangement commonly utilized by women. In U.S. Pat. No. 2,871,859, issued to Dunn on Feb. 3, 1959, there is shown a typical belt-napkin device of this type. A common problem in the use of sanitary napkins for women has been the inability of many of the prior art devices to prevent the napkin from shifting from the desired position, with discomfort and irritation frequently resulting. Arrangements of this type, however, have not previously been utilized for positioning a dressing in the perineal area of a man, and also generally have not provided for the urethral opening of a woman to remain uncovered.

SUMMARY OF THE INVENTION

One embodiment of the present invention is an article of manufacture for positioning in the perineal area of a person which comprises a pad including a layer of absorbent material integral with the pad and sized to fit within the perineal area of the person, said pad having a front end and a rear end, a support member having a first end integrally connected to the rear end of said pad and further having a second end, and a pair of straps, each strap having a first end and a second end, the first ends being integrally connected to the front end of said pad at spaced apart locations, the front end of said pad and said straps defining an opening for permitting passage therethrough of male external genitalia.

It is an object of the present invention to provide a surgical dressing which completely covers the perineal area and which includes an opening capable of permitting the passage therethrough of the male external genitalia or for leaving the urethral opening of a woman uncovered.

It is another object of the present invention to provide a surgical dressing which may be held securely in the perineal area regardless of the user's posture and body movement.

A further object of the present invention is to provide a surgical dressing of the above-described type which fits comfortably and which will not abrade or irritate the skin.

Another object of the present invention is to provide a surgical dressing of the above-described type which may be maintained generally flat against the body of the wearer and which therefore will afford a maximum usefulness of the absorbent portion of the dressing.

It is a further object of the present invention to provide a surgical dressing of the aforementioned type which may be easily installed and removed, and which may be easily disposed of as required.

A still further object of the present invention is to provide a surgical dressing as described which enables the wearer to urinate without needing to remove the dressing.

Another object of the present invention is to provide a surgical dressing of the described type which may be adapted to be adjusted to fit wearers of different sizes.

Further objects and advantages of the present invention will become apparent from the following description and accompanying drawings.

BRIEF DESCRIPTION OF THE DRAWINGS

FIG. 1 is a perspective view of the surgical dressing arrangement of the present invention, showing generally the position of the dressing in respect to the body of the person wearing the device.

FIG. 2 is a top, plan view of an embodiment of the surgical dressing of the present invention.

FIG. 3 is a side, elevational view of the surgical dressing of FIG. 2.

FIG. 4 is a top, plan view of an alternate embodiment of the surgical dressing of the present invention.

FIG. 5 is a side, plan view of the surgical dressing of FIG. 4.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIG. 1, there is shown a surgical dressing arrangement 10 according to the present invention. Dressing 10 includes belt 11 and pad 12 which is secured thereto. Secured to the rear end 32 of pad 12 is support member 18 which is attached to belt 11 by fastener 25. Secured to the front end of pad 12 are straps 15 and 16, which include absorbent portions 13 and 14, respectively. Straps 15 and 16 are attached to belt 11 by fasteners 23 and 24, respectively. Fasteners 23-25 may be of any suitable type, such as spring-tensioned clips or a snap fasteners. Alternatively, straps 15 and 16 and support member 18 could include slots within which belt 11 is received. Specific examples of suitable fastening devices are disclosed in U.S. Pat. Nos. 2,871,859, issued to Dunn on Feb. 3, 1959; 2,684,673, issued to Lerman on July 27, 1954; and, 2,545,224, issued to Butler on Mar. 13, 1951, all of which are hereby incorporated by reference for their disclosure of these exemplary fastening arrangements. Similarly, belt 11 may include any suitable method for facilitating the installment or removal of the belt, and also the adjustment of the size of the belt to fit the wearer. Thus, belt 11 may include a hook fastener 19 which secures together loop portions 20 and 21 of belt 11. Further, a buckle 22 may be included to permit adjustment of the size of the belt 11.

Dressing 10 is sized and shaped to fit securely and comfortably in the perineal area or region of the wearer's body. For the present purposes, the perineal area is defined to extend forwardly to the base of the scrotum for a male person, and forwardly to the urethral opening of a female person, and in either case include the anal region. The dressing of the present invention is particularly suited to use in post-operative cases in which perineal or anorectal surgery has been performed, or in other cases in which it is desired to position an absorbent dressing in the perineal region. For these purposes, pad 12 includes an integral layer of absorbent material which is sized and shaped to fit the perineal region. The absorbent material may be of any type suitable for maintaining a clean environment at the site, and may generally comprise any of the dressings presently employed for such purposes. A gauze material with suitable filler is a preferred type of absorbent material. It is preferable that the absorbent material be of a type which will not cause discomfort or irritation to the skin of the wearer, and also should be sufficiently inexpensive that it may be disposed of periodically.

Pad 12 is preferably a rectangular shape with the front end 29 positionable adjacent the base of the scrotum. Straps 15 and 16 are attached at the front corners of pad 12 and preferably extend generally parallel to the sides of pad 12. Absorbent portions 13 and 14 of straps 15 and 16, respectively, preferably comprise integral extensions of the absorbent layer of pad 12. Support member 18 is also preferably rectangular in shape with sides which extend generally colinear with the sides of rectangular pad 12.

Straps 15 and 16 are attached to the front end 29 of pad 12 at spaced apart locations. Pad 12 and absorbent portions 13 and 14 of straps 15 and 16, respectively, thereby define an opening 17 suitable for passage therethrough of the male external genitalia and equally suitable for leaving uncovered the urethral opening of a female person. The straps are thus spaced apart a sufficient distance 28 to flank and comfortably accommodate therebetween the male genitalia or the female urethral opening. Straps 15 and 16 are provided with a sufficient length 30, generally about 4–8 inches, to properly position pad 12 and opening 17. As shown in the figures, each of the pair of straps is about twice as long as the pad.

Referring in particular to FIGS. 5 and 6, there is shown an alternate embodiment 31 of the surgical dressing of the present invention. Dressing 31 comprises a generally rectangular pad 33 including an integral layer of absorbent material, pad 33 being sized to fit within the perineal region of the wearer. Straps 36 and 37 are attached to the front end 34 of pad 33 and are spaced apart a distance 38 sufficient to provide a suitable opening 35 therebetween. Support member 18 is suitably attached to the rear end of pad 33.

In either of the embodiments shown, the straps and support member may comprise individual members suitably secured to pad 33, such as by stitching or similar means. Alternatively, the straps and support member may be integral with a non-absorbent layer of material which forms an integral part of the pad. Thus, pad 12 or 33 may include a layer of a continuous sheet of flexible material which is secured to the absorbent layer and which extends from the pad to form the straps and support member.

While there have been described above the principles of this invention in connection with specific apparatus, it is to be clearly understood that this description is made only by way of example and not as a limitation in the scope of the invention.

What is claimed is:

1. An article of manufacture for positioning in the perineal area of a person which comprises:
   a pad including a layer of absorbent material integral with the pad and sized to fit within the perineal area of the person, said pad having a front end and a rear end;
   a support member having a first end integrally connected to the rear end of said pad and further having a second end; and
   a pair of straps, each strap having a first end and a second end, the first ends being integrally connected to the front end of said pad at spaced apart locations, the front end of said pad and said straps defining an opening for permitting passage therethrough of male external genitalia, each of said straps including a first portion adjacent the first end, each of the first portions of said straps including a layer of absorbent material integral with the layer of absorbent material of said pad.

2. The article of claim 1 in which said pad further includes a layer of non-absorbent material, said support member and said straps being integral with the non-absorbent material and forming extensions thereof.

3. The article of claim 1 and additionally including means for securing the second ends of said support member and said straps to the body of the person to hold said pad in position.

4. The article of claim 1 in which the layer of absorbent material on each of the first portions of said straps is integral with the layer of absorbent material of said pad.

* * * * *